US00PP22422P2

(12) United States Plant Patent
Pierce

(10) Patent No.: US PP22,422 P2
(45) Date of Patent: Dec. 27, 2011

(54) ***CALIBRACHOA* PLANT NAMED 'CAL ROOSALL'**

(50) Latin Name: *Calibrachoa hybrida*
Varietal Denomination: Cal Roosall

(75) Inventor: Robert O. Pierce, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 7 days.

(21) Appl. No.: 12/804,452

(22) Filed: Jul. 22, 2010

(51) Int. Cl.
*A01H 5/00* (2006.01)

(52) U.S. Cl. ..... Plt./413

(58) Field of Classification Search ..... Plt./413, Plt./356.21

See application file for complete search history.

*Primary Examiner* — June Hwu
(74) *Attorney, Agent, or Firm* — S. Matthew Edwards

(57) ABSTRACT

A new *Calibrachoa* plant named 'Cal Roosall' particularly distinguished by the medium-large, red-purple flower color, small, medium green foliage, and very well-branched, tight, and mounding plant habit.

1 Drawing Sheet

Latin name of the genus and species of the plant claimed: *Calibrachoa hybrida.*

Varietal denomination: 'Cal Roosall'.

BACKGROUND OF THE NEW PLANT

The present invention comprises a new *Calibrachoa,* botanically known as *Calibrachoa hybrida,* and hereinafter referred to by the variety name 'Cal Roosall'.

'Cal Roosall' is a product of a planned breeding program. The new cultivar has medium-large, red-purple flower color, small, medium green foliage, and very well-branched, tight, and mounding plant habit.

'Cal Roosall' originated from a hybridization made in August 2005 in a controlled breeding environment in Gilroy, Calif. USA. The female parent was the unpatented, proprietary plant designated '1543-1' with deep rose-red flowers, is later to flower, and has fewer flowers.

The male parent of 'Cal Roosall' was an unpatented, proprietary plant designated '1512-1', with coral rose flowers, longer internodes, and has a more upright habit. The resultant seed was sown in February 2006.

'Cal Roosall' was selected as one flowering plant within the progeny of the stated cross in May 2006 in a controlled environment in Gilroy, Calif. USA.

The first act of asexual reproduction of 'Cal Roosall' was accomplished when vegetative cuttings were propagated from the initial selection in May 2006 in a controlled environment in Gilroy, Calif. USA.

BRIEF SUMMARY OF INVENTION

Horticultural examination of plants grown from cuttings of the plant initiated in May, 2006, and continuing thereafter, has demonstrated that the combination of characteristics as herein disclosed for 'Cal Roosall' are firmly fixed and are retained through successive generations of asexual reproduction.

'Cal Roosall' has not been observed under all possible environmental conditions. The phenotype may vary significantly with variations in environment such as temperature, light intensity and day length.

Plant Breeder's Rights for this cultivar were applied for in Canada on Feb. 25, 2010 (#10-6866) and in CVPO on Jun. 29, 2010 (#2010/1304). 'Cal Roosall' has not been made publicly available more than one year prior to the filing of this application.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawing shows typical flower and foliage characteristics of 'Cal Roosall' with colors being as true as possible with an illustration of this type. The photographic drawing shows a flowering potted plant of the new variety and a close-up of the flowers.

DETAILED BOTANICAL DESCRIPTION

The aforementioned photographs were taken in April 2010 from plants growing in a greenhouse trial in Gilroy, Calif. USA. These plants were growing in 4 inch pots and were approximately 15-16 weeks of age.

The plant descriptions and measurements were taken in mid-May 2010 in Hillscheid, Germany on 9 week old plants that had been planted into 12 cm pots in mid March and were grown without pinching, on benches in a greenhouse at a minimum temperature (heating temperature) of 12° C.

Color references are made to The Royal Horticultural Society Colour Chart (R.H.S.) 2001.

TABLE 1

DIFFERENCES BETWEEN THE NEW VARIETY 'CAL ROOSALL' AND A SIMILAR VARIETY

| | 'Cal Roosall' | 'Cal Blurose' (U.S. Plant Pat. No. 18,399) |
|---|---|---|
| Flower color: | RHS N66B with a ring around the throat opening of about RHS N57A but little more red | RHS N74B |

TABLE 1-continued

DIFFERENCES BETWEEN THE NEW VARIETY 'CAL ROOSALL' AND A SIMILAR VARIETY

| | 'Cal Roosall' | 'Cal Blurose' (U.S. Plant Pat. No. 18,399) |
|---|---|---|
| Flower size: | Larger | Smaller |
| Foliage color: | Lighter green | Darker green |
| Flowering habit: | Earlier and more center flowering | Later and less center flowering |

Plant:

*Form, growth and habit.*—Compact and mounding with semi-upright stems; well-branched, but pinching enhances the number of branches.

*Plant height.*—9.5-12.0 cm.

*Plant height (inflorescence included).*—About 11-13 cm.

*Plant width.*—18-21 cm.

*Time to produce a flowering plant.*—About 7-8 weeks for a 12 cm pot.

Roots:

*Number of days to initiate roots and produce a rooted cutting.*—25-28 days at about 22 degrees C.

*Type.*—Fine, fibrous, free branching.

*Color.*—RHS 158D.

Foliage:

*Arrangement.*—Alternate, simple.

*Immature, leaf color, upper surface.*—RHS 137D.

*Lower surface.*—Between RHS 143B and RHS 144A.

*Mature, leaf color, upper surface.*—RHS 137C.

*Lower surface.*—RHS 137D.

*Length.*—2.9-3.5 cm.

*Width.*—1.1-1.3 cm.

*Shape.*—Narrowly elliptical.

*Base shape.*—Acuminate.

*Apex shape.*—Obtuse.

*Margin.*—Entire.

*Texture, upper surface.*—Dense short hair.

*Lower surface.*—Dense short hair mostly along the veins and margins.

*Color of veins, upper surface.*—RHS 144A.

*Color of veins, lower surface.*—RHS 144B.

*Petiole color.*—RHS 144C to RHS 145A.

*Length.*—0.1-0.3 cm.

*Diameter.*—0.2 cm.

*Texture.*—Dense short hairs.

Stem:

*Quantity of main branches per plant.*—16-20.

*Color of stem.*—RHS 145A with some small patches of a little anthocyanins of about RHS 177B.

*Length of stem.*—7-11 cm.

*Diameter.*—0.15-0.2 cm.

*Length of internodes.*—0.4-1.1 cm.

*Texture.*—Various sized hairs; glandular hairs.

Pedicel:

*Color of pedicel.*—RHS 137D.

*Length of pedicel.*—1.9-2.5 cm.

*Diameter of pedicel.*—0.1 cm.

*Texture of pedicel.*—Dense hairs; glandular hairs.

Inflorescence:

*Type.*—Flowers solitary in upper leaf axis; flowers face mainly horizontally, mostly 5 fused lobes forming a funnel to salver shaped flower. Continuous flowering throughout the Summer.

*Quantity of inflorescences per plant.*—15-20.

*Lastingness of individual blooms on the plant.*—About 7-9 days.

*Fragrance.*—None.

Bud (just when starting to show color):

*Color.*—RHS N79B.

*Length.*—2.9-2.2 cm.

*Width.*—0.5-0.6 cm.

*Shape.*—Oblong.

Immature inflorescence:

*Color of petals, upper surface.*—RHS N66A.

*Color of petals, lower surface.*—RHS 71D.

Mature inflorescence:

*Flower horizontal diameter.*—3.3-3.8 cm.

*Flower height (vertical).*—1.7-2.2 cm.

*Color of petals, upper surface.*—Closest to RHS N66B with a ring around the throat opening of about RHS N57A but little more red.

*Color of petals, lower surface.*—RHS 72C to RHS 72D.

*Apex shape.*—Truncate.

*Margin.*—Entire.

*Waviness of petals.*—Weak to medium.

*Petal lobation.*—Moderate.

*Petal texture.*—Papillose.

*Corolla tube color outside.*—RHS 154C to RHS 153D with fine dark veins of RHS 177A.

*Inside.*—RHS 7A with weak veins of RHS 152A.

*Corolla texture, outside.*—Papillose and short hairs along the veins.

*Inside.*—Papillose.

Sepals:

*Color, upper surface.*—RHS 137A to RHS 137B but slightly lighter basally.

*Lower surface.*—RHS 137C to RHS 137D.

*Length.*—1.5-1.8 cm.

*Width.*—0.5-0.7 cm.

*Shape.*—Lanceolate.

*Apex shape.*—Obtuse to acute.

*Based.*—Fused.

*Margins.*—Entire.

*Texture, upper surface.*—Glandular hairs of various lengths.

*Lower surface.*—Glandular hairs of various lengths.

Reproductive organs:

*Pistil.*—1.

*Length.*—1.3 cm.

*Style color.*—RHS 145B.

*Style length.*—0.8-0.9 cm.

*Stigma color.*—RHS 144B.

*Stamens.*—5.

*Color of filaments.*—RHS 4D.

*Length filaments.*—0.7-1.1 cm.

*Anther color.*—RHS 8A.

*Anther length.*—0.1 cm.

*Anther shape.*—Elliptical.

*Color of pollen.*—RHS 13B.

*Pollen amount.*—Moderate.

*Fertility/seed set.*—Has not been observed on this hybrid.

Disease/pest resistance: Disease/pest resistance has not been observed on this hybrid.

What is claimed is:

1. A new and distinct variety of *Calibrachoa* plant named 'Cal Roosall' substantially as illustrated and described herein.

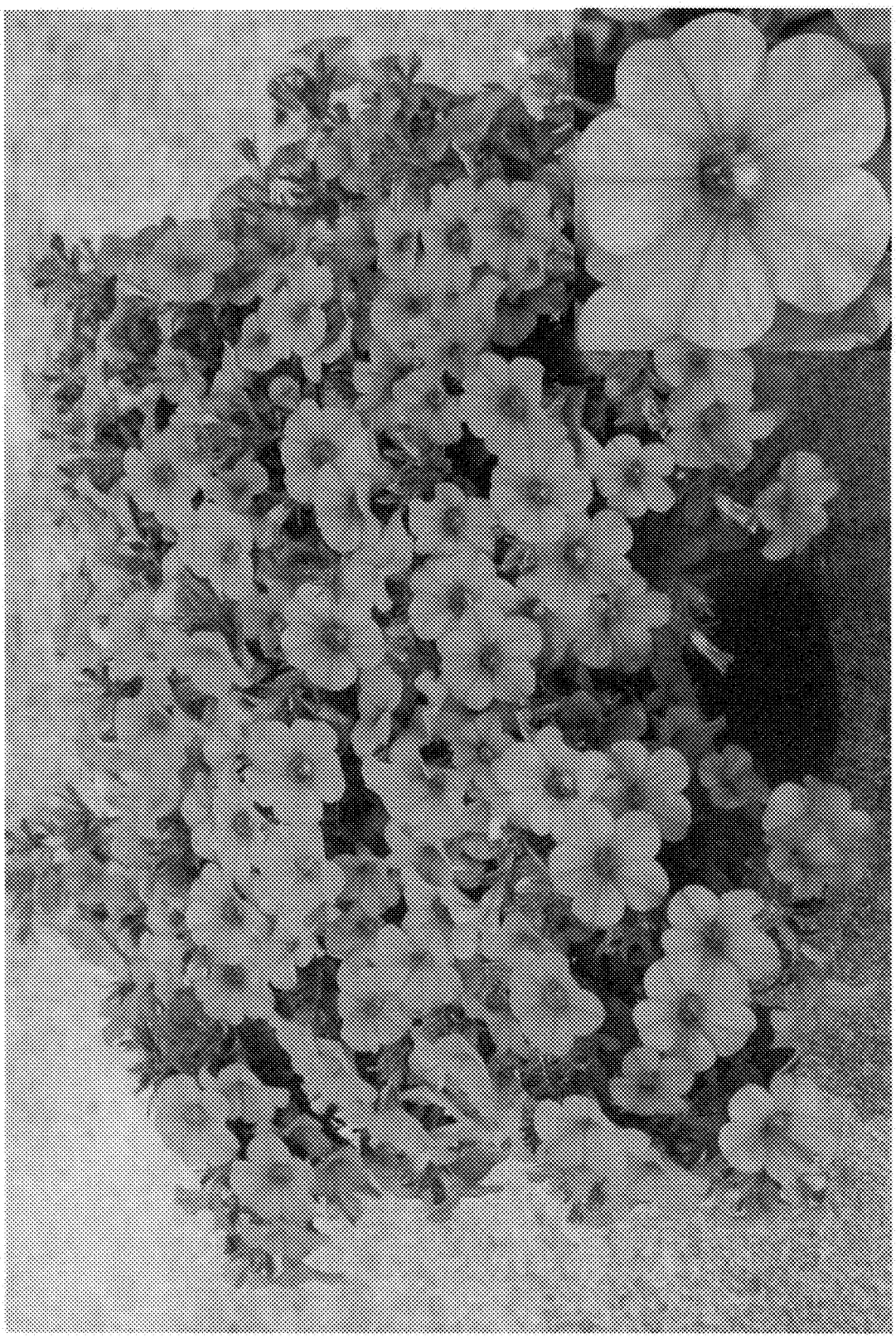

* * * * *